United States Patent [19]
Mortier et al.

[11] Patent Number: 5,899,892
[45] Date of Patent: May 4, 1999

[54] CATHETER HAVING DISTAL FIBER BRAID

[75] Inventors: Todd J. Mortier, Minneapolis; James R. Pray, New Hope; Robert M. Vidlund, Eden Prairie; David A. Kusz, Minneapolis; Cyril J. Schweich, Jr., St. Paul, all of Minn.

[73] Assignee: SciMed Life Systems, Inc., Maple Grove, Minn.

[21] Appl. No.: 08/966,131

[22] Filed: Nov. 7, 1997

Related U.S. Application Data

[63] Continuation of application No. 08/656,163, May 31, 1996, Pat. No. 5,730,733.

[51] Int. Cl.⁶ .................................................. A61M 25/00
[52] U.S. Cl. ............................................................ 604/280
[58] Field of Search ................................. 604/280, 281, 604/282, 50, 51, 264

[56] References Cited

U.S. PATENT DOCUMENTS

| | | | |
|---|---|---|---|
| 2,857,915 | 10/1958 | Sheridan | 128/349 |
| 3,228,894 | 1/1966 | Jeckel | 252/478 |
| 3,370,587 | 2/1968 | Vizcarra | 128/214.4 |
| 3,485,234 | 12/1969 | Stevens | 128/2 |
| 3,608,555 | 9/1971 | Greyson | 128/348 |
| 3,612,038 | 10/1971 | Halligan | 128/2.05 |
| 3,618,614 | 11/1971 | Flynn | 128/348 |
| 3,746,003 | 7/1973 | Blake et al. | 128/349 |
| 3,749,134 | 7/1973 | Slingluff et al. | 138/177 |
| 3,866,599 | 2/1975 | Johnson | 128/2 |
| 3,890,977 | 6/1975 | Wilson | 128/418 |
| 3,935,857 | 2/1976 | Co | 128/2.05 |
| 3,995,623 | 12/1976 | Blake et al. | 128/2.06 |
| 4,015,601 | 4/1977 | Bokros et al. | 128/214 |
| 4,024,873 | 5/1977 | Antoshkiw et al. | 127/349 |
| 4,029,104 | 6/1977 | Kerber | 128/348 |
| 4,099,425 | 7/1978 | Moore | 74/501 |
| 4,117,836 | 10/1978 | Erikson | 128/2.05 |

(List continued on next page.)

FOREIGN PATENT DOCUMENTS

| | | |
|---|---|---|
| 0 208 787 B1 | 8/1992 | European Pat. Off. . |
| 0 517 075 A1 | 12/1992 | European Pat. Off. . |
| 0 643 979 A1 | 3/1995 | European Pat. Off. . |
| 0 358 117 B1 | 5/1995 | European Pat. Off. . |
| WO 92/15356 | 9/1992 | WIPO . |
| WO 94/18886 | 9/1994 | WIPO . |

OTHER PUBLICATIONS

"Progressive Suppleness Pursil Catheter: A New Tool For Superselective Angiography and Embolization", by Jacques E. Dion, Gary R. Duckwiler, Pedro Lytyk, Fernando Vinuela, and John Bentson, *American Journal of Neuroradiology*, Sep./Oct. 1989, pp. 1068–2070.

"Zephyr Flow–Assisted Infusion Catheter", Target Therapeutics, Jul. 1993.

"The BALT Extrusion Family of Magic infusion Catheters", Target Therapeutics, Jul. 1993.

Mallincrodt Medical brochure, in Japanese language, published prior to Jun., 1995.

"Zephyr Flow–Assisted Infusion Catheter", Target Therapeutics, 4/93.

"Magic Catheter 3F/1.8", F BALT, published prior to Jun., 1995.

Pediatric Magic 3F/1.5F Catheter, Balt, published prior to Jun., 1995.

Balt Magic Standard & 1.5F Shaft Configurations data sheet, by Target Therapeutics, 47201 Lakeview Blvd., Fremont, CA 94538, Apr. 1993.

"Injectable Flow–Guided Coaxial Catheters for Selective Angiography and Controled Vascular Occlusion", by Charles T. Dotter, M.D., Josef Rosch, M.D., Paul C. Lakin, M.D., Robert C. Lakin, B.A., and Jack E. Pegg, R.T., *Work in Progress*, pp. 421–423, Aug. 1972.

*Primary Examiner*—John D. Yasko
*Attorney, Agent, or Firm*—Westman, Champlin & Kelly, P.A.

[57] ABSTRACT

A catheter includes a manifold and a proximal shaft portion coupled to the manifold. A distal shaft portion is coupled to a distal end of the proximal shaft portion and is flexible relative to the proximal shaft portion. A fiber reinforcement layer is disposed about the distal shaft portion.

13 Claims, 8 Drawing Sheets

U.S. PATENT DOCUMENTS

| | | | |
|---|---|---|---|
| 4,169,464 | 10/1979 | Obrez | 128/657 |
| 4,184,497 | 1/1980 | Kolff et al. | 131/213 |
| 4,196,731 | 4/1980 | Laurin et al. | 128/214 |
| 4,265,276 | 5/1981 | Hatada et al. | 138/177 |
| 4,276,874 | 7/1981 | Wolvek et al. | 128/1 |
| 4,279,252 | 7/1981 | Martin | 128/349 |
| 4,306,566 | 12/1981 | Sinko | 128/658 |
| 4,329,993 | 5/1982 | Lieber et al. | 128/349 |
| 4,345,602 | 8/1982 | Yoshimura et al. | 128/349 |
| 4,361,152 | 11/1982 | Patel | 604/99 |
| 4,362,163 | 12/1982 | Krick | 604/280 |
| 4,368,730 | 1/1983 | Sharrock | 604/158 |
| 4,385,635 | 5/1983 | Ruiz | 128/658 |
| 4,425,919 | 1/1984 | Alston, Jr. et al. | 128/658 |
| 4,464,176 | 8/1984 | Wijayarathna | 604/164 |
| 4,504,268 | 3/1985 | Herlitze | 604/170 |
| 4,547,193 | 10/1985 | Rydell | 604/282 |
| 4,571,240 | 2/1986 | Samson et al. | 604/96 |
| 4,577,543 | 3/1986 | Wilson | 87/11 |
| 4,596,563 | 6/1986 | Pande | 604/264 |
| 4,610,674 | 9/1986 | Suzuki et al. | 604/282 |
| 4,627,844 | 12/1986 | Schmitt | 604/264 |
| 4,639,246 | 1/1987 | Dudley | 604/158 |
| 4,694,838 | 9/1987 | Wijayarthna et al. | 128/658 |
| 4,696,304 | 9/1987 | Chin | 128/673 |
| 4,721,115 | 1/1988 | Owens | 128/713 |
| 4,737,153 | 4/1988 | Shimamura et al. | 604/282 |
| 4,739,768 | 4/1988 | Engelson | 128/658 |
| 4,747,840 | 5/1988 | Ladika et al. | 604/281 |
| 4,758,221 | 7/1988 | Jureidini | 604/95 |
| 4,762,130 | 8/1988 | Fogarty et al. | 128/348.1 |
| 4,775,371 | 10/1988 | Mueller, Jr. | 604/280 |
| 4,817,613 | 4/1989 | Jaraczewski et al. | 128/658 |
| 4,840,622 | 6/1989 | Hardy | 604/264 |
| 4,842,590 | 6/1989 | Tanabe et al. | 604/282 |
| 4,883,058 | 11/1989 | Ruiz | 128/654 |
| 4,884,579 | 12/1989 | Engelson | 128/772 |
| 4,898,591 | 2/1990 | Jang et al. | 604/282 |
| 4,960,410 | 10/1990 | Pinchuk | 604/96 |
| 4,963,306 | 10/1990 | Weldon | 264/101 |
| 4,985,022 | 1/1991 | Fearnot et al. | 604/282 |
| 4,994,069 | 2/1991 | Ritchart et al. | 606/191 |
| 5,019,057 | 5/1991 | Truckai | 604/282 |
| 5,037,404 | 8/1991 | Gold et al. | 604/282 |
| 5,057,092 | 10/1991 | Webster, Jr. et al. | 604/282 |
| 5,069,673 | 12/1991 | Schwab | 604/280 |
| 5,069,674 | 12/1991 | Fearnot et al. | 604/282 |
| 5,078,702 | 1/1992 | Pomeranz | 604/280 |
| 5,085,649 | 2/1992 | Flynn | 604/282 |
| 5,088,991 | 2/1992 | Weldon | 604/280 |
| 5,116,652 | 5/1992 | Alzner | 428/36.9 |
| 5,156,785 | 10/1992 | Zdrahala | 264/108 |
| 5,171,232 | 12/1992 | Castillo et al. | 604/280 |
| 5,221,255 | 6/1993 | Mahurkar et al. | 604/43 |
| 5,221,270 | 6/1993 | Parker | 604/282 |
| 5,234,416 | 8/1993 | Macaulay et al. | 604/282 |
| 5,248,305 | 9/1993 | Zdrahala | 604/280 |
| 5,254,107 | 10/1993 | Soltesz | 604/282 |
| 5,279,596 | 1/1994 | Castaneda et al. | 604/282 |
| 5,286,259 | 2/1994 | Ganguly et al. | 604/96 |
| 5,294,325 | 3/1994 | Liu | 204/418 |
| 5,306,262 | 4/1994 | Weldon | 604/281 |
| 5,308,342 | 5/1994 | Sepetka et al. | 604/282 |
| 5,314,418 | 5/1994 | Takano et al. | 604/282 |
| 5,334,169 | 8/1994 | Brown et al. | 604/282 |
| 5,336,205 | 8/1994 | Zenzen et al. | 604/280 |
| 5,342,386 | 8/1994 | Trotta | 606/194 |
| 5,348,536 | 9/1994 | Young et al. | 604/43 |
| 5,356,388 | 10/1994 | Sepetka et al. | 604/164 |
| 5,380,304 | 1/1995 | Parker | 604/282 |
| 5,397,306 | 3/1995 | Nobuyoshi et al. | 604/96 |
| 5,403,292 | 4/1995 | Ju | 604/282 |
| 5,472,435 | 12/1995 | Sutton | 264/282 |
| 5,484,565 | 1/1996 | Larsen et al. | 264/230 |

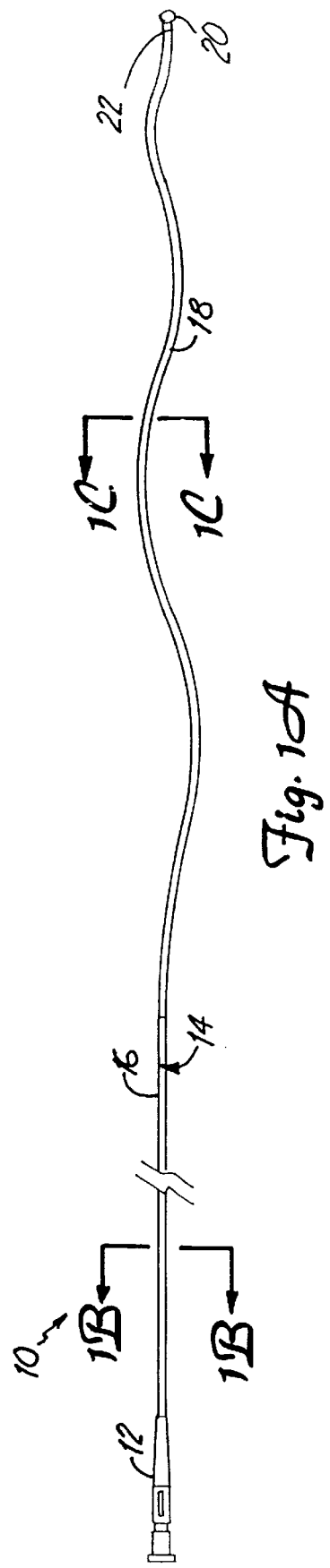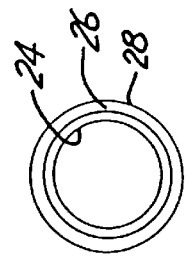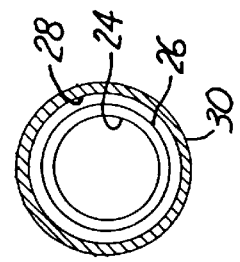

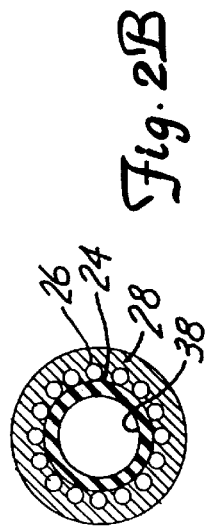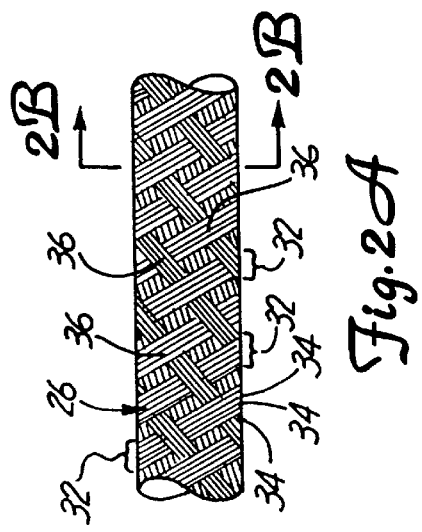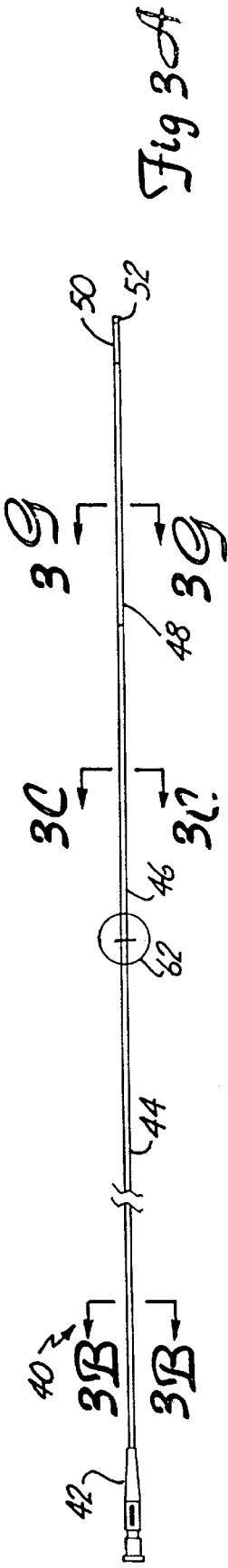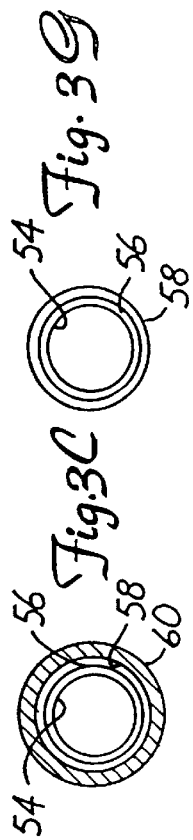

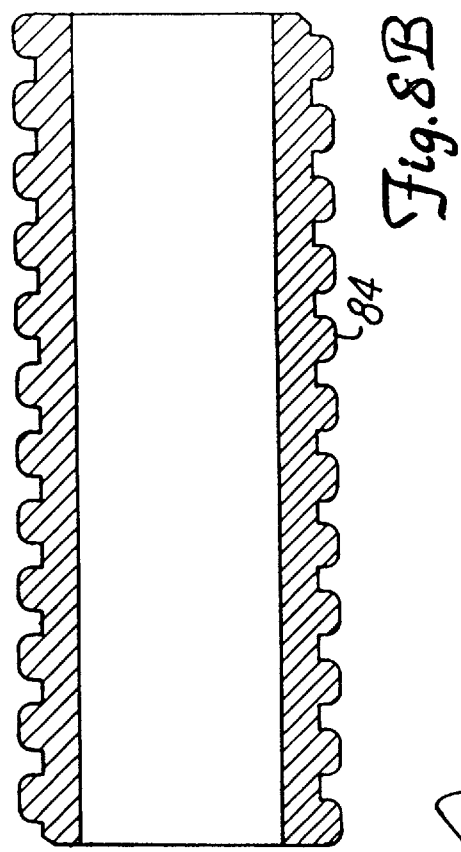
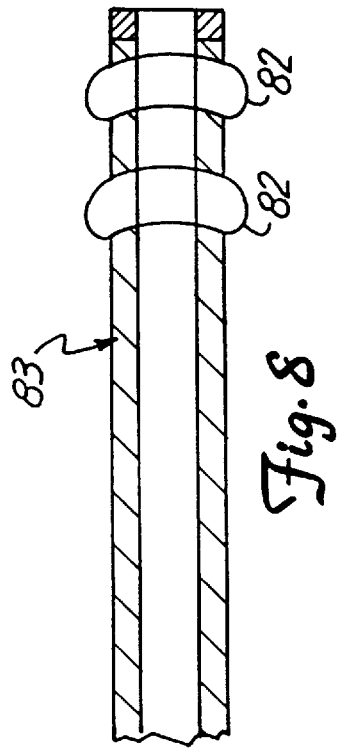
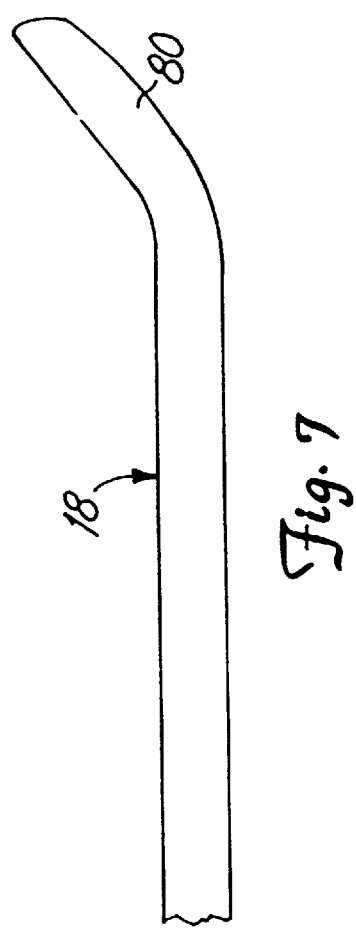

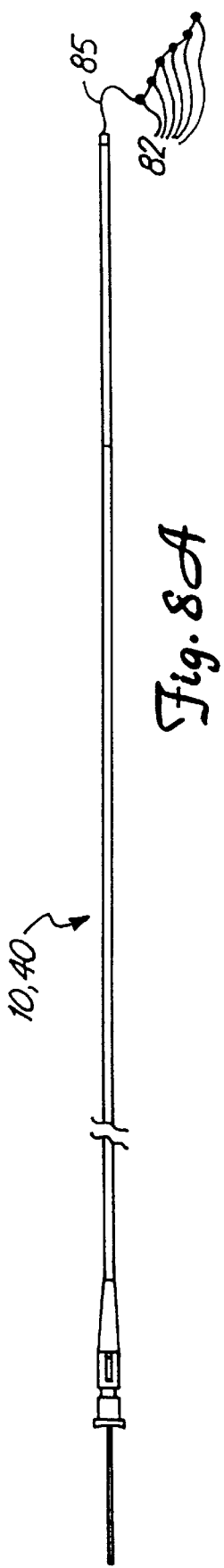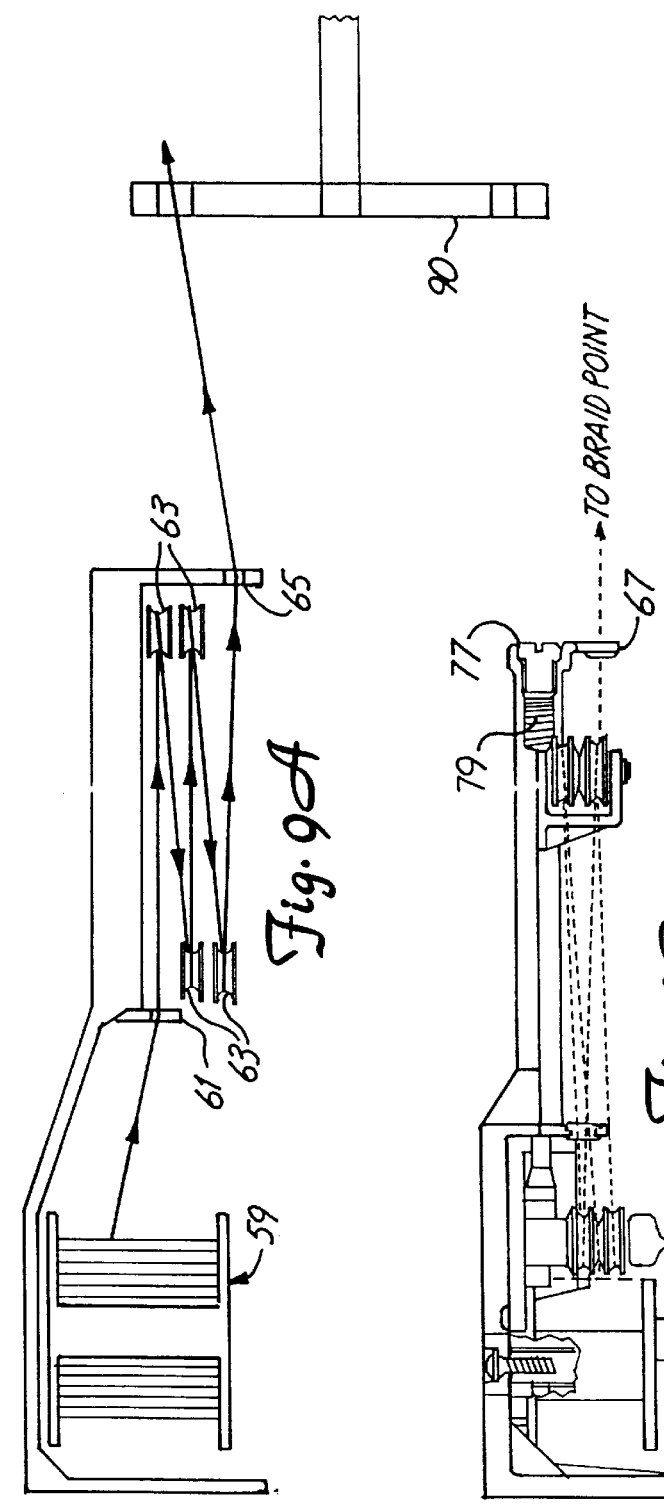
Fig. 8A
Fig. 9A
Fig. 9B

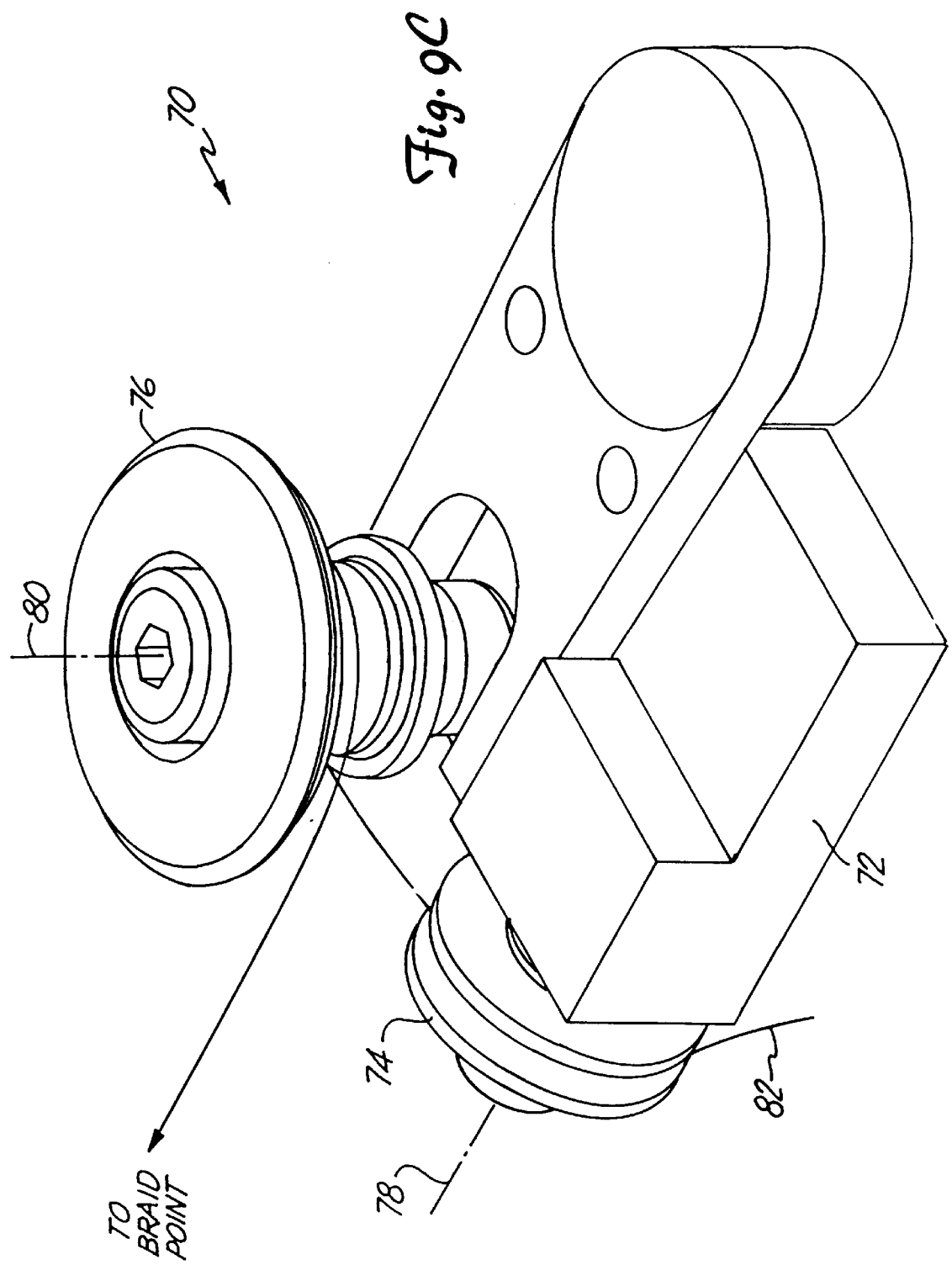

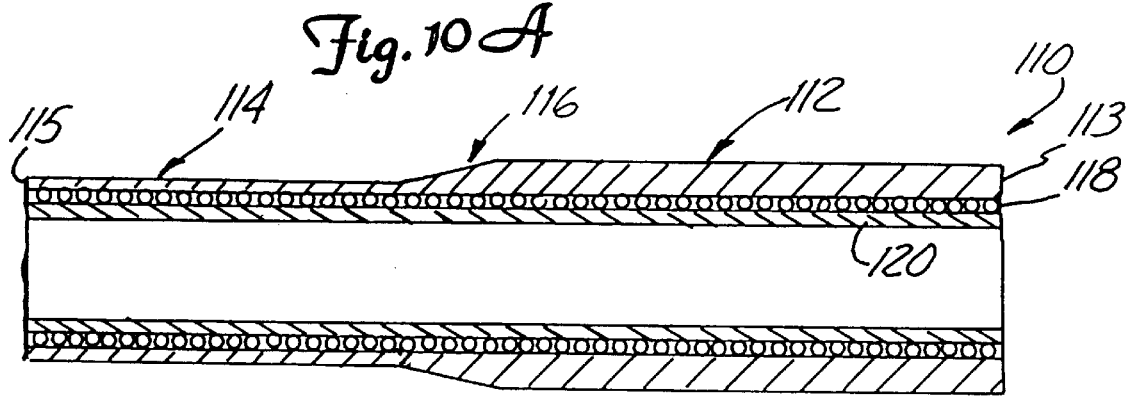
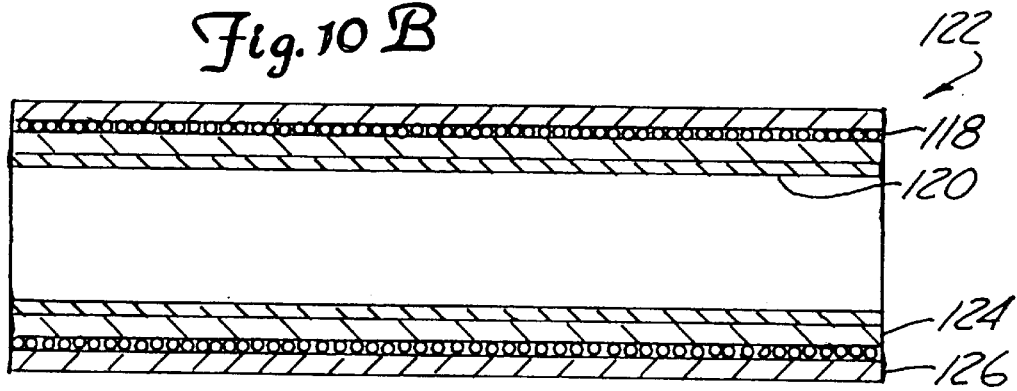
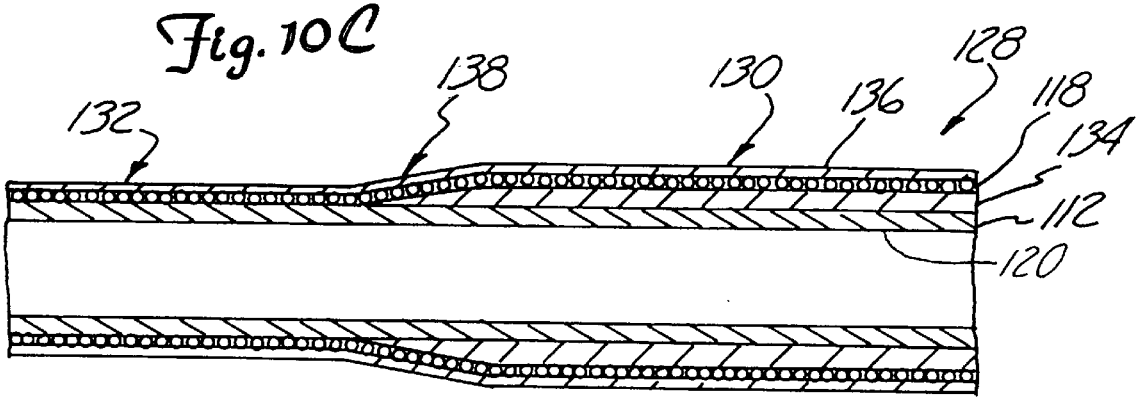

CATHETER HAVING DISTAL FIBER BRAID

This is a continatuation of application Ser. No. 08/656,163, filed May 31, 1996, now U.S. Pat. No. 5,730,733.

BACKGROUND OF THE INVENTION

The present invention deals with medical tubes. More particularly, the present invention deals with medical tubes, such as catheters.

Flow directed or flow assisted catheters are catheters which are used to access extremely tortuous vasculature, such as neuro vasculature. Conventional, over-the-wire catheters can also be used, but exhibit limitations in their ability to reach and maneuver within such intricate vasculature. Therefore, the flow assisted catheter is used.

Flow assisted catheters typically have a distal portion which is extremely flexible. Some flow assisted catheters also typically have an inflatable balloon or bulbous member at their distal ends. The flow assisted catheter is inserted into a vessel to be accessed through a guide catheter, and fluid may typically be pulsed through the guide catheter to carry the flow assisted catheter into the desired vessel. Once in the vessel, the flow assisted catheter is drawn through the vessel (primarily by blood flow) and is fed into the vessel by the physician. If the catheter has a balloon, the balloon is inflated to increase the drag between the blood flowing in the vessel and the distal end of the flow assisted catheter. The balloon is essentially carried by the flow through the vasculature to a target site. This draws the catheter along to the target site.

If the distal tip of the catheter becomes frictionally engaged with a vessel wall, or becomes "hung up" at a vessel branch, slack develops in the catheter. The physician then slightly withdraws the catheter until the catheter has moved away from the vessel wall or branch and is again free to move within the vessel. Once flow has taken up all the slack, the physician then feeds additional catheter length into the vessel.

In addition, some prior flow directed catheters included bent (typically steam formed) tips at the distal end of the flow directed catheter. This has been done in an effort to provide some selective tracking of the flow directed catheter into a desired vessel branch.

Current flow directed catheters suffer from a number of disadvantages. The distal portion of the flow directed catheter must be extremely flexible so that it is capable of tracking the intricate vasculature to the site to be accessed under the influence of flow in the vessel. Consequently, conventional flow directed catheters have had distal portions formed of material which is extremely flexible, and which is also quite soft. Typically, the softer the material, the lower the burst pressure. Thus, some conventional flow assisted catheters are formed with distal shaft portions with undesirably low burst pressure. This can cause the catheter to burst when injectate is introduced through the catheter.

Further, soft materials commonly have undesirably low tensile strength and also tend to stick to the vessel wall. This can cause the catheter to hang up in the vessel more often. When withdrawing the catheter to disengage it from the vessel wall, or when removing the catheter from tortuous vasculature, a catheter with such low tensile strength is susceptible to breakage.

In addition, when the physician is feeding the catheter into the vessel, the highly flexible distal portion of the conventional flow directed catheter can accumulate slack and loop. Then, when the treating physician withdraws the flow directed catheter, it can easily kink.

Further, the flexible nature of the distal portion of conventional flow directed catheters makes it virtually non-torquable by the treating physician. In other words, if the treating physician rotates or torques the proximal end of the flow directed catheter, the distal portion of the flow directed catheter is so flexible, and has such low torsional rigidity, that the torque does not transfer to the distal end. The physician must over-rotate the proximal end of the catheter, withdraw the catheter a short distance, allow the catheter to advance in the vessel and hope for some unpredictable amount of torque at its distal end. This makes selective tracking very difficult and cumbersome, even when the catheter includes a shaped tip.

The inability to transfer torque, in itself, leads to another significant problem as well. When the flow directed catheter hangs up in the vessel, the attending physician cannot break the friction between the catheter and the vessel wall by simply torquing the catheter. Rather, as described above, the physician must withdraw the flow directed catheter to some extent so it disengages from the vessel wall. Repeatedly withdrawing and advancing the flow directed catheter causes the treating physician to take an undesirable amount of time in accessing the target vasculature.

Also, in order to make the catheters highly flexible, they are often made with a very small diameter. This results in very low flow rates of injectate through the catheter and also makes it particularly difficult, if not impossible, to use such catheters to deliver large particles or coils. Finally, the soft materials used with such catheters are not typically compatible with some agents, such as alcohol. This is undesirable since a physician may wish to deliver alcohol with such a catheter.

SUMMARY OF THE INVENTION

A catheter includes a manifold and a proximal shaft portion coupled to the manifold. A distal shaft portion is coupled to a distal end of the proximal shaft portion and is flexible relative to the proximal shaft portion. A fiber reinforcement layer is disposed about the distal shaft portion.

BRIEF DESCRIPTION OF THE DRAWINGS

FIG. 1A is a side view of a flow directed catheter according to the present invention.

FIGS. 1B and 1C are cross-sectional views of the catheter shown in FIG. 1.

FIG. 2A is a side view of a portion of a braid according to the present invention.

FIG. 2B is a cross-sectional view of the braid shown in FIG. 2A.

FIG. 3A is a side view of a second embodiment of a flow directed catheter according to the present invention.

FIGS. 3B, 3C, 3D, 3E, 3F and 3G are cross-sectional views of the catheter shown in FIG. 3A.

FIG. 7 is another embodiment of a tip portion of a catheter according to the present invention.

FIG. 8 is another embodiment of a tip portion of a catheter according to the present invention.

FIG. 8A shows another embodiment of a tip portion of a catheter according to the present invention.

FIG. 8B shows a contoured surface of a catheter according to the present invention.

FIGS. 9A and 9B show a portion of a conventional braiding machine.

FIG. 9C illustrates a modified assembly mounted on the braiding machine shown in FIGS. 9A and 9B.

FIGS. 10A–10C illustrate a plurality of other embodiments implementing features of the present invention.

DETAILED DESCRIPTION OF THE PREFERRED EMBODIMENTS

Figure 3F:
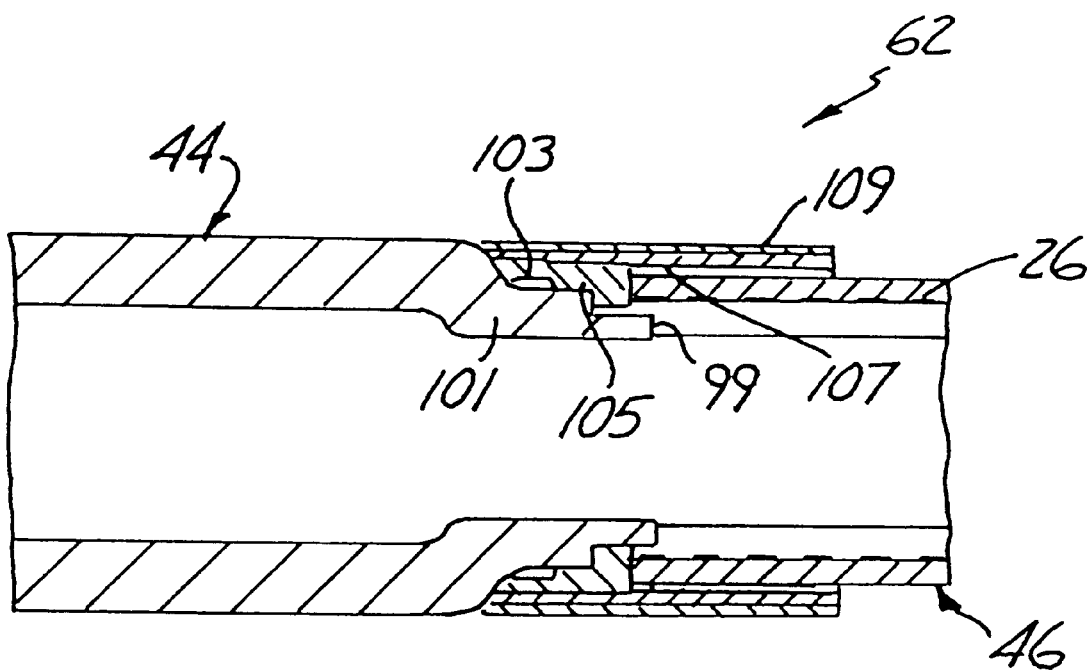

FIG. 1A is a side view of one preferred embodiment of a flow directed catheter 10 according to the present invention. Catheter 10 includes manifold 12 and shaft 14. Shaft 14 includes proximal shaft portion 16 and distal shaft portion 18. Distal shaft portion 18, has, at its distal end, tip 20. Catheter 10 also includes marker band 22 which is formed of radiopaque material that can be observed under fluoroscopy.

In a preferred embodiment, catheter 10, from manifold 12 to tip 20 is roughly 100–200 cm in length. In addition, distal shaft portion 18 is preferably approximately 45 cm to 55 cm in length.

Proximal shaft portion 16 is formed to be rigid relative to distal shaft portion 18. Distal shaft portion 18, on the other hand, is extremely flexible and suitable for being assisted or directed through a vessel in the human body by blood flow. Bulbous tip 20 is provided to increase the drag between the blood flowing in the vessel and catheter 10. While catheter 10 can be used without tip 20, the increased drag provided by tip 20 allows the blood flow to assist in tracking the catheter to the vascular site to be accessed.

It is also desirable (although not necessary) that proximal shaft 16 have relatively high torsional rigidity so that it transmits a large portion of torque applied by the administering physician to distal shaft portion 18. Also, it is preferred that proximal shaft portion 16 be relatively stiff or rigid in the axial direction so that the treating physician can insert shaft portion 16 into a guide catheter simply by pushing on shaft portion 16.

It is important that distal shaft portion 18 be extremely flexible so that it can be carried through tortuous vasculature. However, it is also very important that distal shaft portion 18 be strong in both tensile strength and burst strength. Further, it is desirable that distal shaft portion 18 have relatively high torsional rigidity (also referred to as torsional stiffness) to transmit torque applied by a treating physician through manifold 12 or proximal shaft portion 16.

FIG. 1B is a cross-section of shaft portion 16 taken along section lines 1B—1B in FIG. 1A. The outer diameter of proximal shaft portion 16 is approximately 2.8 French. FIG. 1B shows that proximal shaft portion 16 is formed of a number of layers. Proximal shaft portion 16 has an undercoat layer 24 which defines the inner lumen of catheter 10. Undercoat layer 24 is preferably urethane, PVC polyamide, or silicon. Proximal shaft portion 16 also includes a reinforcement layer shown in FIG. 1B as braid layer 26. The braid layer 26 is described in more detail with respect to FIGS. 2A and 2B. Briefly, however, braid layer 26 is formed of fibers braided about layer 24 to add strength to, and increase the torsional rigidity of, proximal shaft portion 16. After braid layer 26 is disposed about layer 24, overcoat layer 28, similar to layer 24, is coated onto braid layer 26.

Layer 28 is also formed of urethane, PVC, polyamide, or silicon. Finally, a stiff jacketing layer 30 is provided over layer 28. Stiff jacketing layer 30 is formed of relatively stiff material (e.g., having an elastic modulus greater than 10,000 psi) such as polyimide, PVC, polyethylene or PET. Such a configuration provides proximal shaft portion 16 with a relatively stiff or rigid characteristic, and with a high degree of strength.

FIG. 1C is a cross-section of distal shaft portion 18 taken along section lines 1C—1C in FIG. 1A. FIG. 1C shows that distal shaft portion 18 is preferably formed of undercoat layer 24, braid layer 26 and overcoat layer 28 shown in FIG. 1B, which simply extend continuously from within stiff jacketing layer 30. In this way, distal shaft portion 18 is highly flexible, yet the braid layer 26 provides distal shaft portion 18 with very high burst pressure, tensile strength and torsional rigidity.

FIG. 2A illustrates a portion of braid layer 26 in greater detail. FIG. 2A illustrates that braid layer 26 is formed of a number of different fibers 32, each fiber comprising a plurality of individual filaments 34. In the preferred embodiment, braid layer 26 is formed of eight fibers 32, each comprising five filaments 34. Further, in one preferred embodiment, the filaments 34 are formed of a liquid crystal polymer material, such as a material commercially designated as Vectran sold by Hoechst Celanese Corporation of Charlotte, N.C. The filaments 34 are each approximately 20–25 microns in diameter. Five filaments 34 are assembled together to preferably form one 25 Denier fiber 32.

FIG. 2A also shows that, in braid layer 26, the fibers 32 overlap one another at areas referred to as picks 36. The number of picks per longitudinal inch of catheter 10 affect both the burst strength and torsional stiffness of catheter 10. In the preferred embodiment, braid layer 26 has approximately 70–120 picks per longitudinal inch of the catheter.

FIG. 2B is a cross-section of the portion of catheter 10 shown in FIG. 2A and taken along section lines 2B—2B in FIG. 2A. FIG. 2B shows layers 24, 26 and 28 in greater detail. In the preferred embodiment, layers 24 and 28 are formed of a product commercially designated as Desmopan sold by the Polymers Division of Miles Inc. which is located in Pittsburgh, Pa.

FIG. 2B also better illustrates the process of making catheter 10. FIG. 2B shows a copper mandrel or copper core 38 disposed within the inner lumen of catheter 10. In the preferred embodiment, undercoat layer 24 is extruded onto copper mandrel 38. Braid layer 26 is applied to layer 24 and that entire assembly is encased in overcoat layer 28 which is extruded over braid layer 26. To remove mandrel 38, the axial ends of mandrel 38 are pulled in opposite directions. This causes mandrel 38 to neck down to a smaller diameter and break free of undercoat layer 24. Once free, mandrel 38 is removed. On proximal shaft portion 16, stiff jacketing layer 30 is then placed over layer 28 to provide the desired stiffness. In order to place layer 30 over layer 28, the axial ends of the braided shaft are pulled in opposite directions. This causes the braid layer 26 to decrease in diameter. Jacketing layer 30 is then placed over braid layer 26 and the ends of the braid are released. This causes the braided shaft to increase in diameter frictionally engaging jacketing layer 30. Both ends of jacketing layer 30 are then bonded to layer 28.

In another embodiment, layers 28 and 30 are coextruded on braid layer 26. The coextrusion runs substantially the entire length of the catheter. After the catheter has been cut to an appropriate length, the outer, stiffer layer 30 is removed from the distal portion of the catheter by grinding, scraping, or other suitable means. Thus, the catheter has a stiffer proximal portion and a more flexible distal portion with one continuous inner lumen. Manifold 12 is assembled onto proximal shaft portion 16 in any suitable, known manner.

The extrusion process used in forming the present invention preferably utilizes the above-described over core extrusion technique. The core material utilized for the shaft according to the present invention is preferably an annealed copper. The core may be preheated prior to the first extrusion pass. Preheating prior to the second extrusion pass may also be used to possibly improve adhesion between the layers.

FIG. 3A is a preferred embodiment of a catheter 40 according to the present invention. catheter 40 includes manifold 42, proximal shaft portion 44, midshaft portion 46, distal shaft portion 48 and flexible tip portion 50. Flexible tip portion 50 is also provided with a radiopaque marker band 52 which is visible under fluoroscopy. As with catheter 10, catheter 40 is preferably approximately 160–165 cm in length from manifold 42 to marker band 52. Also, midshaft portion 46 and distal shaft portion 48, along with flexible tip portion 50, are approximately 45 cm to 55 cm in total length. The particular length of midshaft portion 46 and distal shaft portion 48 will vary depending on the particular application in which catheter 40 is used.

In the preferred embodiment, proximal shaft portion 44 is relatively rigid or stiff, midshaft portion 46 is a transition portion which is more flexible than proximal shaft portion 44, but less flexible than distal shaft portion 48. Distal shaft portion 48 is highly flexible, similar to distal shaft portion 18 of catheter 10 shown in FIG. 1A. Flexible tip portion 50 has even greater flexibility than distal shaft portion 48.

FIG. 3B is a cross-sectional view of catheter 40 taken along section lines 3B—3B in FIG. 3A. FIG. 3B shows that proximal shaft portion 44 is formed of a single, relatively stiff, material such as polyimide or polyurethane. In the preferred embodiment, the outer diameter of proximal shaft portion 44 is approximately 2.8 French.

FIG. 3C is a cross sectional view of catheter 40 taken along section lines 3C—3C in FIG. 3A. In the preferred embodiment, midshaft portion 46 has an inner diameter in a range of approximately 0.010 inches to 0.022 inches. Midshaft portion 46 preferably has approximately the same outer diameter as proximal shaft portion 44.

FIG. 3C shows that midshaft portion 46 is substantially formed of four layers. Layers 54, 56 and 58 are similar to layers 24, 26 and 28 shown in FIGS. 1B and 1C. In other words, an undercoat 54 of polyurethane (preferably Desmopan) is first extruded and then a braid layer 56 (preferably formed of strands of Vectran fiber) is braided onto layer 54. Then, an overcoat layer 58 (also preferably of polyurethane or Desmopan) is extruded over braid layer 56. FIG. 3C also shows that midshaft portion 46 has an outer layer 60 which provides midshaft portion 46 with a stiffness that is preferably intermediate that of proximal shaft portion 44 and distal shaft portion 48. Outer layer 60, in the preferred embodiment, is a polyurethane material commercially designated as Texin 5286 (or other suitable material) which is necked or drawn over layer 58. In other words, layer 60 is placed over layer 58 and drawn through a heated die. In another embodiment, layer 60 is first swelled, then placed over layer 58 and then shrunk to fit over layer 58. Texin is commercially available from the Polymers Division of Miles Inc. of Pittsburgh, Pa.

In another preferred embodiment, the layers of catheter 40 can be formed using the coextrusion and grinding process described above with respect to catheter 10.

Figure 3D:
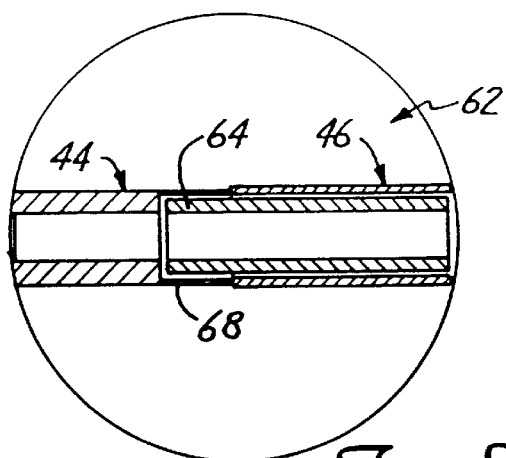

FIG. 3D is a detailed cross-sectional view of a joint portion 62 between proximal shaft portion 44 and midshaft portion 46. Midshaft portion 46 has a proximal end 64 which includes only layers 54, 56 and 58 shown in FIG. 3C. In other words, outer layer 60 is removed. Distal end 68 of proximal shaft portion 44 has a portion removed from the inner diameter thereof to form an enlarged receiving aperture. The inner diameter of the enlarged receiving aperture in end 68 of proximal shaft portion 44 is sized just larger than the outer diameter of the proximal end portion 64 of midshaft portion 46. Therefore, end 64 of midshaft portion 46 fits snugly within end 68 of proximal shaft portion 44. Further, any suitable adhesive or fastening technique can be used to secure end 64 within end 68.

Figure 3E:
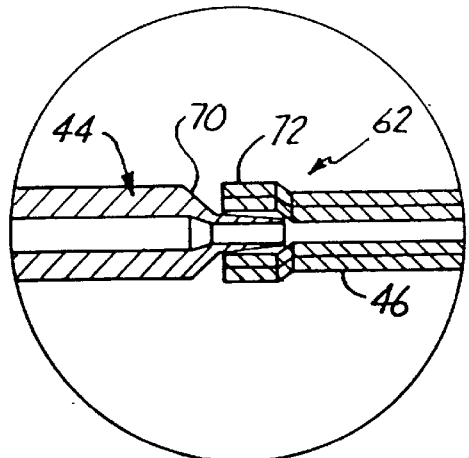

FIG. 3E is another preferred embodiment of joint portion 62 joining midshaft portion 46 to proximal shaft portion 44. In the embodiment shown in FIG. 3E, proximal shaft portion 44 has a tapered distal end 70 which reduces to a small outer diameter. Midshaft portion 46, by contrast, has an expanded proximal end portion 72 which expands to have an inner diameter just larger than the outer diameter of tapered end portion 70 of proximal shaft portion 44. Tapered end portion 70 fits snugly within the inner diameter of expanded end portion 72 and, as in the embodiment shown in FIG. 3D, any suitable, commercially available adhesive or fastening technique can be used to couple end 70 to end 72.

FIG. 3F is another preferred embodiment of joint portion 62 joining midshaft portion 46 to proximal shaft portion 44. In the embodiment shown in FIG. 3F, the proximal shaft portion 44 has a tapered distal end 101 which reduces to a small outer diameter. The midshaft portion 46, by contrast, has a notched, or slightly enlarged proximal end 99 which is large enough to have an inner diameter just larger than the outer diameter of tapered end portion 101 of the proximal shaft portion 44. A radiopaque marker band 103 is placed over distal end 101 of proximal shaft portion 44. The manner in which radiopaque marker band 103 is placed over proximal shaft portion 44 is described later in greater detail, with respect to FIG. 4. The marker band 103 is then covered with a urethane adhesive 105. The urethane adhesive 105 is then covered, in turn, by an epoxy adhesive 107 which underlies a polyimide sleeve 109. Sleeve 109 preferably extends through a major portion of joint portion 62 and is adhered to joint portion 62 through epoxy adhesive 107. As with earlier embodiments, adhesives 105 and 107 are preferably commercially available adhesives known in the art.

FIG. 3G is a cross-sectional view of distal shaft portion 48 taken along section lines 3G—3G in FIG. 3A. FIG. 3G shows that distal shaft portion 48 is formed of only layers 54, 56 and 58. Therefore, distal shaft portion 48 is extremely flexible, yet has high tensile strength and burst strength.

Figure 4:
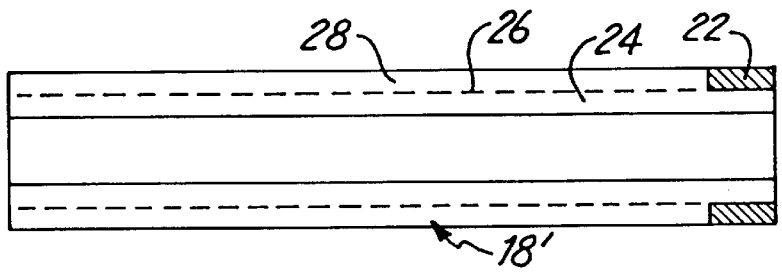
FIG. 4 illustrates one embodiment of a tip portion of a catheter according to the present invention.

FIG. 4 is a cross-sectional view of one embodiment of a distal tip 18' suitable for use with either catheter 10 shown in FIG. 1A or catheter 40 shown in FIG. 3A. FIG. 4 shows that the tip portion is formed similarly to the distal shaft portion 18 shown in FIG. 1C. Radiopaque marker band 22 is provided at the very distal end of the shaft portion 18' and, in the embodiment shown in FIG. 4, the enlarged bulbous tip 20 is removed.

Figure 5:
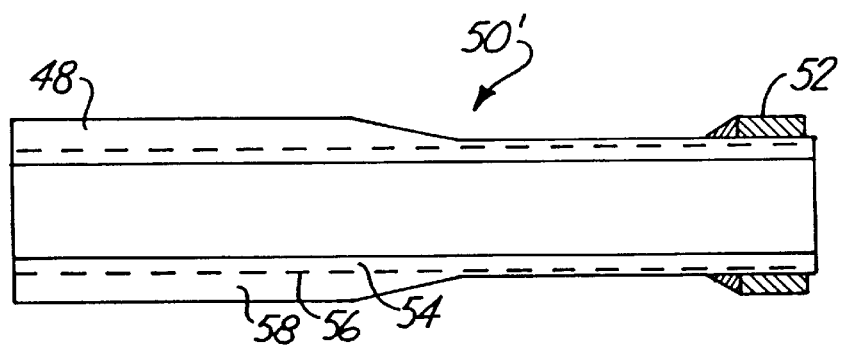
FIG. 5 shows a second embodiment of a tip portion of a catheter according to the present invention.

FIG. 5 shows a second embodiment of a distal tip 50' suitable for use as tip 50 shown in FIG. 3A. FIG. 5 shows that tip portion 50' has a tapered outer layer 58 to which marker band 52 is adhesively secured. The length of tapered tip 50' is, in one preferred embodiment, approximately 2–3 cm. Tip 50' has tapered overcoat layer 58 to provide even greater flexibility than the remainder of distal shaft portion 48.

Figure 6:
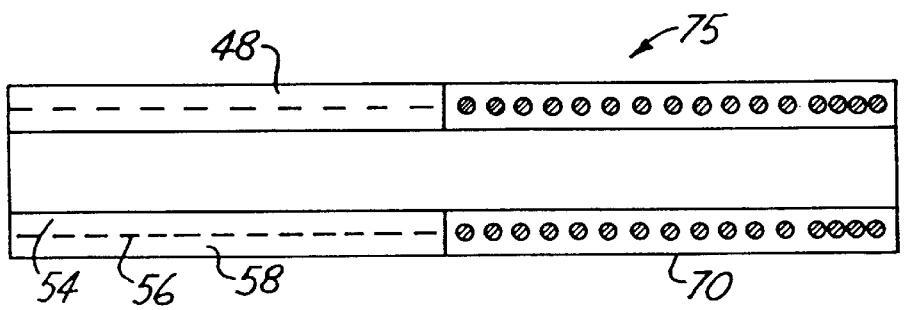
FIG. 6 shows a third embodiment of a tip portion of a catheter according to the present invention.

FIG. 6 is a cross-sectional view of yet another embodiment of a distal tip 75 suitable for use with either catheter 10 or catheter 40. FIG. 6 shows tip 75 attached to shaft portion 48 of catheter 40. In FIG. 6, a metal coil 70 (which is preferably formed of a radiopaque material such as platinum) is secured to the distal end of distal shaft portion 48. Coil 70 is preferably formed of 0.001–0.002 inch platinum wire and is therefore radiopaque. Coil 70 is preferably encased by placing it on undercoat layer 54 and dipping coil 70 into dissolved encasing material.

FIG. 7 shows another embodiment of a distal tip of a catheter 10, 40 according to the present invention. Tip 80 is preferably heat or steam shapeable, along with layers 26, 56. It should be noted that tip 80 can either be integrally formed with catheter 10, 40 simply as the distal end thereof, or it can be formed separately and connected to catheter 10, 40.

The curved shape improves tracking because tip 80 does not dive into the outer radius of a vessel bend as it approaches the bend. Rather, tip 80 reaches the outer curvature of the bend and, when properly oriented by the physician, slides along the bend. Bent tip 80 only provides this significant advantage if it can be oriented properly within the vessel. In conventional flow directed catheters, the torsional rigidity (and hence torque transfer) is very low and orientation of tip 80 was very difficult. Since braided layers 26 and 56 are provided in catheters 10, 40 according to the present invention, rotating the proximal shaft provides a very predictable rotation at the distal portion of the shaft. This significantly increases selective tracking of the flow directed catheter 10, 40 and improves catheter advancement.

Tip portion 80 also increases pressure drag within the vessel. In other words, since tip 80 is bent, the friction between tip 80 and the fluid flowing in the vessel is higher than if tip 80 were straight. This further assists in moving the catheter along the vessel.

It should be noted that tip 80 can also be provided in a spiral or squiggle configuration to orient tip 80 into the axis of flow through the vessel thereby increasing drag by increasing the surface area of the shaft exposed to the flow.

FIG. 8 shows a second embodiment of a distal tip portion 83 of shaft 10 or 40 according to the present invention which increases drag of the catheter 10, 40 relative to fluid flowing in the vessel. A plurality of bulbous or balloon members 82 are provided at the distal tip 83. This serves to increase the friction between the flowing fluid in the vessel and the catheter 10, 40. This further assists in catheter advancement. It should be noted that, as shown in FIG. 8A, either of the bulbous members 82, or additional bulbous members 82, can be attached to an extremely flexible thread 85 which is attached to, or run through, the catheter 10, 40. Since thread 85 is even more flexible than the distal portion of the shaft, it assists in tracking through tortuous vasculature and essentially drags the distal tip of the catheter along to the site to be accessed. Also, bulbous member 82 is preferably placed a short distance proximal of the distal tip of the catheter rather than precisely at the distal tip. For example, in the embodiment shown in FIG. 7, bulbous member 82 is preferably placed just proximal of the bend in tip 80. This placement aids in tracking by increasing drag, but does not significantly affect the ability of the distal tip to select small vessels.

FIG. 8B shows yet another embodiment of the present invention utilized to increase drag of the catheter relative to the flow in the vessel. FIG. 8B shows that a contoured shape is provided on the outer surface 84 of the distal end portion of the shaft of catheters 10, 40. Such a contour can be cut or compressibly formed into the outer surface of the shaft using appropriate tooling. Further, such an impression can be made in the outer surface of the shaft utilizing molding techniques.

Braid layers 26 and 56 are preferably applied to extruded layer 54 with commercially available braiding machines. Two such machines which have been used with satisfactory results are the Kokubun No. ST16 Braiding Machine commercially available from Toyota Tsusho America or Kokubun Ltd. from Hamatsu, Japan. A second commercially available system which has been used satisfactorily is one available from Wilhelm Steeger GmbH & Co. type no. K80/16-72/89 Braiding Machine. Wilhelm Steeger GmbH & Co. is located in Barmen, Germany.

Both machines are preferably somewhat modified in order to perform satisfactorily. The machines are typically designed to braid larger gauge fibers than those used with the present invention. The modifications to the machines for adaptation to the present invention focused on the carriers or totes that hold and dispense fiber as they circulate around the inner hub or braid point.

It is important in braiding layers 26 and 56 to have low tension on the fiber and to minimize sliding contact with any parts on the braiding machine which can damage the fibers. Minimizing damage and high tension in the fiber is also important when the fiber is wound on the spools of the braider. Further, ionized air is used in the system in a known manner to control and remove undesirable foreign material during the braiding process.

To better illustrate the modifications to both the Steeger and Kokubun machines, the modifications to a Steeger machine will now be described. FIG. 9A is a schematic view of the operation of the conventional, unmodified, Steeger machine identified above. The fiber is removed from a storage mechanism 59, travels through a first eyelet 61 and is threaded about a plurality of pulleys 63. The fiber is then threaded through a top eyelet 65 and then provided to the braid point or inner hub 90.

FIG. 9B is a side view of a portion of a standard Steeger fiber carrier used in the above-identified braiding machines. It will be noted that the Steeger machine provides a double pulley assembly with a top eyelet 67 through which the fiber travels to the braid point 90. It has been found that eyelet 67 was a source of problems in that it damaged the fiber due to friction and due to surface roughness.

FIG. 9C is one embodiment of a top carrier assembly 70 used in modifying both the Kokubun and Steeger machines. The machine carriers are originally provided with the top eyelet which, as discussed above, caused damage to the fibers. Therefore, assembly 70 is mounted on the top of the carriers to replace the eyelet. Assembly 70 includes mounting block 72, pulley 74 and conical spool 76. Mounting block 72 is assembled onto the top 77 of the carrier (shown in FIG. 9B). Pulley 74 is rotatable about axis of rotation 78 and conical spool 76 is rotatable about axis of rotation 80. The fiber 82 is threaded from the standard lower portion of the machine. However, instead of traveling through eyelet 67, the fiber travels up around pulley 74 and around conical spool 76 and then to the braid point or central hub 90 on the machine.

In the Kokubun machines, the carriers are commonly of nearly all metal construction. A similar combination of eyelets and pulleys are used to guide the fiber through the machine and to control timing during which more fiber is released from a storage spool. However, the eyelets on the Kokubun machine have also been observed to cause damage to the fibers from sliding friction, and breakage of the fibers from surface irregularities on the eyelet. Thus, the Kokubun machine was modified to replace the eyelets with Delrin or Teflon plastic rollers.

Further, the Kokubun machine is provided with only a single pulley system (as opposed to the double pulley system shown on the Steeger machine). This was replaced with a pair of pulleys to reduce the tension in the fiber. By replacing the metal contact portions with plastic parts, significant advantages are achieved. The parts move more quickly because they have smaller mass than the metal parts, and the plastic parts are not slowed down by lubricant which is required in metal part designs.

A spring (79 in FIG. 9B) is provided in the carriers of both Steeger and Kokubun machines which provides the tension for fiber take-up. The take-up spring 79 must provide low enough force to keep tension as low as possible on the fiber, but must be high enough to have a quick response as the carrier weaves in and out along its path around the braid point 90. A preferred tension (the force measured to pull the fiber off of the carrier) is in a range of approximately 20–90 grams.

The pulleys provided with the Steeger machine had observable surface roughness. These pulleys were replaced with pulleys made from ultra high molecular weight polyethylene.

The number of picks per inch provided by the braid, and the number of elements in the braid, affect both flexibility and strength. In other words, the higher the pick count, the stronger the catheter (with respect to both burst pressure and tensile strength), and the more torsional rigidity is exhibited by the catheter.

FIGS. 10A–10C illustrate other embodiments of the present invention. In FIG. 10A, a cross section of a portion of a catheter 110 is shown. Catheter 110 has improved lumen characteristics in order to, for example, deliver embolic materials. Catheter 110 has a shaft which includes a distal section 112 and a proximal section 114. Sections 112 and 114 are connected by a transition point 116. Proximal section 112 is formed by extrusion of a stiffening layer 113, such as polyimide, polyamide, or polyurethane. Distal section 114 has an outer layer 115 which is also extruded and is preferably a material which is more flexible than layer 113 at proximal section 112. Outer layer 115 is preferably formed of polyurethane. Transition point 116 defines a portion of catheter 110 in which the changeover in the extruder head from material comprising proximal section 112 to the material comprising distal section 114 occurs. Therefore, the material in transition point 116 is a combination of those two materials.

Catheter 110 also includes a braid layer 118 which is similar to that described in the previous embodiments. Catheter 110 is also provided with an inner lining 120. Inner lining 120 is preferably constructed of a material which is lubricous and chemically resistant, such as polytetraflouroethylene (PTFE), polyethylene (PE) or fluorinated ethylene polymer (FEP). This material provides a more lubricous layer to aid in guide wire insertion and manipulation, and it also aids in the passage of solid embolic materials, such as platinum coils and PVA particles. Because these tend to be relatively stiff material (i.e., where the elastic modulus E is on the order of 30,000–120,000), the layer must be thin so as not to make the shaft of the catheter too stiff. Therefore, it is preferred that the layer be less than approximately 0.001 inches, and more preferably between approximately 0.0003 inches and 0.0004 inches. Lubricious coating 120 may be on only a portion of catheter 110 (such as the proximal or distal portion) or the different portions of the catheter can have different lubricious coatings thereon.

FIG. 10B shows a cross section of a portion of another catheter 122 according to the present invention which includes the lubricous coating 120 shown in FIG. 10A. However, catheter 122 simply has braid layer 118 sandwiched between two polyurethane encasement layers 124 and 126. These layers are preferably formed as described previously in which layer 124 is extruded, braid layer 118 is applied, and layer 126 is extruded thereover. As with the embodiment shown in FIG. 10A, inner lining 120 is preferably extruded or applied in any suitable way.

FIG. 10C shows another embodiment of the present invention in which a portion of catheter 128 is shown in cross section. Catheter 128 includes a proximal section 130 and a distal section 132. Proximal section 130 includes the lubricous inner lining 120 described in the embodiments shown in both FIGS. 10A and 10B. However, catheter 128 also includes, at proximal section 130, an extruded selective stiffening layer 134 which is preferably formed of polyimide, polyamide, or polyurethane. The braid layer 118 is disposed over stiffening layer 134, and a top coat 136 of polyurethane or polyamide material is also extruded over braid 118. Selective stiffening layer 134 has relatively high rigidity to provide the proximal section 130 with relatively greater stiffness than distal section 132.

Between proximal section 130 and distal section 132 is a transition section 138. Transition section 138 includes all of the layers described with respect to proximal section 130 except that the extrusion of stiffening layer 134 is tapered off to zero. This provides for transition section 138 having a rigidity which is intermediate that of proximal section 130 and distal section 132. Distal section 132 is formed of the same layers as proximal section 130, except that stiffening layer 134 is no longer present. Therefore, while distal section 132 is highly flexible, proximal section 130 is relatively rigid.

The present invention provides means by which a great deal of flexibility can be maintained in the catheter, without sacrificing torsional rigidity, burst pressure levels, or tensile strength. It has been found that, utilizing the present invention, a preferred ratio of burst pressure to flexibility is in a range greater than approximately 60,000. The present invention has been used to provide shafts with a ratio of burst pressure to flexibility in a range of approximately 130,000 to in excess of 500,000.

In these examples, burst pressure was measured using a commonly known technique. One end of the shaft to be measured was closed off and the interior of the shaft was pressurized with a measurable source, until a discontinuity or fault (such as a hole) developed in the shaft. The pressure was measured in pounds per square inch (psi).

Flexibility measurements are referred to in terms of the elastic modulus (E) and were taken using a cantilevered method. One end of the shaft was held in place and the other end was deflected. A measurement of the force required to deflect the sample beam (or cantilevered shaft) a certain distance was measured. The elastic modulus (E) was calculated as follows:

$$E = Fl^3 / 3I_z y \qquad (EQ.\ 1)$$

where F=force;

l=the length of cantilever;

$I_z$=the moment of inertia (for a tube $I_z = \pi/64\ [d_o^4 - d_i^4]$, where $d_o$ is the outer diameter of the tube and $d_i$ is the inner diameter); and y=vertical deflection.

For a one half inch length of shaft, the ratio F/y measured was 0.0009 pounds per inch of deflection. From this, E can be calculated using the above equation 1. For example: E=0.0009(0.5³)/3 (π64(0.029⁴−0.019⁴))=1324 psi.

Using these techniques, the ratio of burst pressure to flexibility in one preferred embodiment was measured at in excess of 400,000, and has been observed to be as high as 700,000. The shafts used had dimensions of 0.019 inch inner diameter and 0.029 inch outer diameter. Smaller shafts having an inner diameter of 0.012 inches and an outer diameter of 0.023 inches have also been successfully manufactured, and the ratios of burst pressure to flexibility are approximately in the same ranges as indicated above.

The shaft manufactured according to the present invention, including braid layer 26, has also been observed to have an elastic modulus in the range of approximately 400 psi to 4,000 psi using standard ASTM elastic modulus test procedures.

Torsional rigidity or torsional stiffness, as used herein, is determined as follows:

$$\text{Torsional stiffness} = M/\phi = GI_z/L \qquad (EQ.\ 2)$$

where M=moment;

φ=angle of twist (in radians);

G=shear modulus;

$I_z$=moment of inertia; and

L=length of sample.

To compare different tubes, independent of dimensions, the shear modulus (G) was first calculated using test results. The test included twisting the sample tube and measuring the moment. The shear modulus can be calculated using the following formula:

$$\text{Shear modulus} = G = ML/\phi I_z \qquad (EQ.\ 3)$$

To express the relationship between torsional properties and flexibility, the ratio of the shear modulus to the elastic modulus (G/E) was used. The elastic modulus was calculated as set out above. The ratio of G/E for conventional flow assisted catheters is approximately 0.21. The ratio of G/E using the reinforced shaft according to the present invention yields a value in excess of 0.25, more preferably above 0.75 and has been observed to be in a preferred range above 1.25 and approximately 1.8–2.6. This is a significant enhancement over prior flow assisted devices.

Another way to express the relationship between burst pressure and flexibility is to express it in terms of a ratio of ultimate hoop stress (σ) and elastic modulus. Using the formula for hoop stress in a cylinder with uniform internal radial pressure:

$$\sigma = qb^2(a^2+r^2)/(r^2(a^2-b^2)) \qquad (EQ.\ 4)$$

Where

σ=normal stress in the circumferencial direction (hoop stress);

q=unit pressure;

a=outer radius;

b=inner radius; and r=radius to point (a>r>b).

Using the point of maximum normal circumferential stress (r=b) yields the formula:

$$\sigma_{max} = q(a^2+b^2)/(a^2-b^2) \qquad (EQ.\ 5)$$

Using current methods, the average burst pressure of the tube is approximately 350 psi and burst pressures as high as 500 psi have been observed.

Substituting these numbers into the maximum hoop stress equation 5 yields:

$$\sigma_{350} = 876.5\ lb/in^2\ \text{and} \qquad (EQ.\ 6)$$

$$\sigma_{500} = 1252\ lb/in^2$$

Calculating a modulus for the tube using F/y=0.0009, inner diameter=0.091 inches, and outer diameter=0.029 inches yields 1324 lb/in².

Now calculating the ratio of maximum hoop stress at burst to elastic modulus ($\sigma_{max}/E$), yields:

$$\sigma_{350}/E = 0.662\ \text{and}\ \sigma_{500}/E = 0.946 \qquad (EQ.\ 7)$$

This can be compared to test results for prior 1.8 French catheters (such as the Balt Magic catheter) in which:

$$\sigma_{max}/E = 0.15\ \text{and} \qquad (EQ.\ 8)$$

(for the Target Zephyr catheter, assuming 200 psi burst) $\sigma_{max}/E = 0.18$.

Because incorporation of the braided fiber layers 26 and 56 in the shaft provide a significant increase in torsional rigidity (and thus torque transfer characteristics) the treating physician can break any friction which develops between the shaft and the vessel wall. This converts friction in the system from static friction to lower dynamic friction which results in further and more smooth tracking.

Because the braid fibers are formed of a number of filaments, the fibers lay down on the tubular surface over which they are braided to provide a thin braid band. This increases the surface coverage of the shaft over which the braids are disposed, but maintains the wall thickness of the shaft within desirable limits. This improves burst characteristics. Further, braiding provides the shaft with a relatively low elongation percent (relative to prior flow directed catheters) resulting in less ballooning or radial expansion of the shaft during use.

Also, since torsional rigidity and strength are significantly enhanced, without sacrificing flexibility, the catheter according to the present invention can be made with an inner diameter significantly larger than prior art catheters. The present invention allows satisfactory operation of catheters with an inner diameter of in excess of 0.015 inches and up to approximately 0.021 inches and preferably in a range of approximately 0.018 inches to 0.019 inches. This allows greater flexibility in the types of injectate, agents, or particles (including coils) which can be administered with the catheter.

Further, while the reinforcing layer according to the present invention has been disclosed in the form of a braided layer, it can also take the form of a tightly wound coil, a mesh sleeve, tapered longitudinal strands, or similar reinforcing configurations incorporated into the catheter.

Finally, it should also be noted that the shaft according to the present invention may be hydrophilically coated. Hydrophilic coating on the shaft reduces friction between the shaft and the vessel wall and thus significantly improves the ability of the shaft to flow in the vessel and track through tortuous vasculature. Placing the hydrophilic coating on the shaft also increases skin drag. Because the coating absorbs water from the blood, it creates a layer of fluid and blood around the outer surface of the shaft that has zero velocity. This increases skin drag and assists in catheter advancement.

Although the present invention has been described with reference to preferred embodiments, workers skilled in the art will recognize that changes may be made in form and detail without departing from the spirit and scope of the invention.

What is claimed is:

1. A catheter, comprising:

a manifold;

a proximal shaft portion coupled to the manifold;

a distal shaft portion coupled to a distal end of the proximal shaft portion and being flexible relative to the proximal shaft portion; and a liquid crystal polymer (LCP) fiber braid disposed about the distal shaft portion wherein the LCP fiber braid includes a plurality of fibers disposed on the distal shaft portion.

2. A catheter, comprising:

a manifold;

a proximal shaft portion coupled to the manifold;

a distal shaft portion coupled to a distal end of the proximal shaft portion and being flexible relative to the proximal shaft portion;

a fiber braid disposed about the distal shaft portion; and a hydrophilic coating disposed about at least the distal shaft portion.

3. A catheter, comprising:

a manifold;

a proximal shaft portion coupled to the manifold;

a distal shaft portion coupled to a distal end of the proximal shaft portion and being flexible relative to the proximal shaft portion;

a fiber braid disposed about the distal shaft portion; and wherein at least a distal end of the distal shaft portion has a conformation suitable to be guided by blood flow within a blood vessel.

4. The catheter of claim 3 wherein the distal end of the distal shaft portion comprises:

a curved tip.

5. The catheter of claim 3 wherein the distal shaft portion has a contoured exterior surface.

6. The catheter of claim 3 wherein the distal shaft portion includes a first bulbous member disposed thereabout.

7. The catheter of claim 6 wherein the distal shaft portion further comprises:

a second bulbous member disposed thereabout.

8. The catheter of claim 3 wherein the distal shaft portion includes an outer surface having at least one protruding ring extending therefrom.

9. The catheter of claim 8 wherein the distal shaft portion includes:

a plurality of outwardly protruding rings extending from the outer surface of the distal shaft portion.

10. A catheter, comprising:

a proximal shaft portion;

a distal shaft portion coupled to a distal end of the proximal shaft portion and being flexible relative to the proximal shaft portion; and a fiber braid coupled to the distal shaft portion, the fiber braid including a plurality of fibers.

11. The catheter of claim 10 wherein the plurality of fibers each comprise a plurality of filaments.

12. The catheter of claim 11 wherein each of the plurality of filaments is formed of a liquid crystal polymer material.

13. The catheter of claim 12 wherein the fiber braid comprises:

eight fibers, each of the eight fibers having five filaments.

* * * * *